United States Patent [19]

Merger et al.

[11] Patent Number: 4,476,316

[45] Date of Patent: Oct. 9, 1984

[54] PREPARATION OF N-SUBSTITUTED CARBAMATES

[75] Inventors: Franz Merger, Frankenthal; Gerhard Nestler, Ludwigshafen, both of Fed. Rep. of Germany

[73] Assignee: BASF Aktiengesellschaft, Ludwigshafen, Fed. Rep. of Germany

[21] Appl. No.: 459,057

[22] Filed: Jan. 19, 1983

[30] Foreign Application Priority Data

Feb. 11, 1982 [DE] Fed. Rep. of Germany ....... 3204711

[51] Int. Cl.$^3$ ................ C07C 125/065; C07C 126/067
[52] U.S. Cl. .................................... 560/024; 560/27; 560/32; 560/132; 560/157; 560/162; 560/163
[58] Field of Search .................... 560/132, 24, 32, 27, 560/157, 162, 163

[56] References Cited

U.S. PATENT DOCUMENTS 4,282,368  8/1981  Merger et al. ...................... 560/24

FOREIGN PATENT DOCUMENTS 1157598  11/1963  Fed. Rep. of Germany .

*Primary Examiner*—Bernard Helfin
*Attorney, Agent, or Firm*—John H. Shurtleff

[57] ABSTRACT

N-Substituted carbamates are prepared by reacting a carbamate with an olefin in the presence of a cation exchanger containing sulfonic acid groups and of from 0.1 to 50 g of an alcohol per mole of starting material II.

The N-substituted carbamates obtainable by the process of the invention are active ingredients and useful starting materials for the preparation of dyes, pesticides and drugs.

20 Claims, No Drawings

PREPARATION OF N-SUBSTITUTED CARBAMATES

The present invention relates to a process for the preparation of N-substituted carbamates by reacting a carbamate with an olefin in the presence of a cation exchanger containing sulfonic acid groups and of from 0.1 to 50 g of an alcohol per mole of starting material II.

German Published Application DAS No. 1,157,598 discloses that, when a carbamate is reacted with an olefin in the presence of an anhydrous mineral acid, an organic sulfonic acid or a Lewis acid, an N-alkylated carbamate is obtained. Concentrated sulfuric acid or boron trifluoride etherate is preferably employed in this process (loc. cit., column 2, pages 22–25 and Examples 1–12). However, this process has the disadvantages that an expensive procedure in which the effluent is polluted is required to separate off the catalyst, and that by-products (telomers of the olefins) are formed and hence low yields (from 10 to 70% of theory) are obtained. Although acidic ion exchangers are mentioned as a class, individual substances, procedures and examples are not described. Chlorohydrocarbons and aromatic and aliphatic hydrocarbons are stated as solvents, but only benzene, toluene and glacial acetic acid are used in the examples. It is also known that the strongly acidic alkylating conditions lead to partial telomerization of the olefins employed. These telomers in turn can react with the carbamate employed, the product being an N-alkylated carbamate (German Published Application DAS No. 1,157,598, column 3, lines 7–10).

German Laid-Open Application DOS No. 2,925,480 discloses a process for the preparation of p-substituted aromatic carbamates by reaction of an aromatic carbamate with an olefin in the presence of an inorganic acid or a sulfonic acid. Cation exchangers containing sulfonic acid groups are also described in detail, and used in Examples. The carbamates always have an aromatic radical as a substituent on the nitrogen atom, which can be monosubstituted or disubstituted. All Examples involve a monosubstituted N-phenylcarbamate. The olefin used does not attack the nitrogen atom but substitutes the aromatic radical, eg. phenyl, in the p-position. It is stated that as a rule no solvent is used; alcohols are not mentioned.

We have found that N-substituted carbamates of the formula $$\begin{array}{ccccc} R^1 & R^2 & H & O & \\ | & | & | & \| & \\ H-C-C-N-C-OR^5 & & & & \quad I \\ | & | & & & \\ R^3 & R^4 & & & \end{array}$$

where the individual radicals $R^1$, $R^2$ and $R^3$ may be identical or different and $R^2$ is always an aliphatic, cycloaliphatic, araliphatic or aromatic radical, $R^4$ is an aliphatic, cycloaliphatic or araliphatic radical or, when $R^2$ is an aromatic radical or a member of an alicyclic, bicyclic or tricyclic radical, may furthermore be hydrogen, in each case 2 or more of the radicals $R^1$, $R^2$, $R^3$ and $R^4$ may furthermore be members of an alicyclic, bicyclic or tricyclic radical, $R^1$ and/or $R^3$ may furthermore be hydrogen, and $R^5$ is an aliphatic, cycloaliphatic or araliphatic radical, are advantageously obtained by reaction of a carbamate with an olefin in the presence of a cation exchanger containing sulfonic acid groups, as a catalyst, if a carbamate of the formula $$\begin{array}{c} O \\ \| \\ H_2N-C-OR^5 \end{array} \quad II$$

where $R^5$ has the above meanings, is reacted with an olefin of the formula $$\begin{array}{cc} R^1 & R^2 \\ | & | \\ C=C \\ | & | \\ R^3 & R^4 \end{array} \quad III$$

where $R^1$, $R^2$, $R^3$ and $R^4$ have the above meanings, in the presence of from 0.1 to 50 g of an alcohol per mole of starting material II.

Where ethyl carbamate and isobutene are used, the reaction can be represented by the following equation:

$$NH_2CO_2C_2H_5 + (CH_3)_2C=CH_2 \longrightarrow H_3C-\underset{\underset{CH_3}{|}}{\overset{\overset{CH_3}{|}}{C}}-NHCO_2C_2H_5$$

Compared to the conventional processes, the process according to the invention surprisingly gives N-substituted carbamates by a simpler and more economical route and in better yield, space/time yield and purity, even when carried out industrially on a large scale. In contrast to the reactions described in German Published Application DAS No. 1,157,598 (see Comparative Examples 1 and 2), in the alkylation according to the invention, in the presence of an alcohol, the formation of olefin oligomers and of the corresponding N-substituted carbamates is substantially prevented. Moreover, it is surprising that in this process neither formation of carbonates nor deactivation (neutralization) of the catalyst by liberated amines takes place, since on the basis of the prior art (The Chemistry of Open-Chain Nitrogen Compounds, vol. 1, page 261 (equation 107), W. A. Benjamin Inc., 1965, New York), instead of the acidic hydrolysis described therein, an acid-catalyzed alcoholysis of the carbamates, in accordance with the following equations, was to be expected:

$$NH_2CO_2R^7 + R^6OH \rightarrow NH_3 + R^6OCO_2R^7$$

$$R^8NHCO_2R^7 + R^6OH \rightarrow R^8NH_2 + R^6OCO_2R^7$$

However, as shown in Examples 5–9, neither deactivation of the catalyst nor formation of carbonates was detected.

Moreover, we have found, surprisingly, that in contrast to German Published Application DAS No. 1,157,598 (column 1, line 38) n-alkenes undergo virtually no reaction under the conditions according to the invention, and it is therefore possible, for example in the preparation of N-tert.-butylcarbamates, to use the substantially cheaper $C_4$ cut. A further advantage of the process is that the catalyst can be separated off in a very simple manner and without polluting the environment, and can be reused as often as desired.

Although German Published Application DAS No. 1,157,598 (column 2, line 19) proposes the use of acidic ion exchangers, no information on the exchangers is given, and it must therefore be assumed that these are the gel-type exchanger resins conventionally used at that time. However, as shown in Comparative Example 11, only unsatisfactory results are obtained when these exchanger resins of gel type are used. It is surprising that such gel catalysts give good results when used in the novel process.

The olefin III can be reacted with the carbamate II in a stoichiometric amount, in excess or in less than the stoichiometric amount, preferably in a ratio of from 0.3 to 5, in particular from 0.5 to 4, moles of olfein III per mole of carbamate II. Preferred carbamates II and olfeins III, and accordingly preferred N-substituted carbamates I, are those of the formulae where the individual radicals $R^1$, $R^2$ and $R^3$ may be identical or different and $R^2$ is always alkyl of 1 to 10, in particular of 1 to 4, carbon atoms, or cycloalkyl of 5 to 8 carbon atoms which is unsubstituted or substituted by alkyl, in particular 1 or 2 alkyl groups, each of 1 to 4 carbon atoms, or is aralkyl of 7 to 12 carbon atoms or phenyl, $R^4$ is alkyl of 1 to 10, in particular 1 to 4, carbon atoms, or cycloalkyl of 5 to 8 carbon atoms which is unsubstituted or substituted by alkyl, in particular 1 or 2 alkyl groups, each of 1 to 4 carbon atoms, or is aralkyl or alkylaryl of 7 to 12 carbon atoms and, when $R^2$ is an aromatic radical or a member of an alicyclic, bicyclic or tricyclic radical, may furthermore be hydrogen, in each case 2 or more of the radicals $R^1$, $R^2$, $R^3$ and $R^4$ may furthermore be members of an alicyclic ring of 5 to 8 carbon atoms or of a bicyclic ring of 7 to 10 carbon atoms or of a tricyclic ring of 10 to 12 carbon atoms, $R^1$ and/or $R^3$ may furthermore be hydrogen, and $R^5$ is alkyl of 1 to 10, in particular 1 to 8, carbon atoms, cycloalkyl of 5 to 8 carbon atoms or aralkyl of 7 to 12 carbon atoms. The aliphatic olefins III are always branched, both $R^2$ and $R^4$ being alkyl. The above radicals and rings can be further substituted by atoms or groups which are inert under the reaction conditions, eg. alkyl or alkoxy of 1 to 5 carbon atoms, chlorine or bromine. The olefins II may contain 2 double bonds, eg. isoprene, limonene and dicyclopentadiene, but as a rule only one double bond of the olefin undergoes reaction, in accordance with the invention.

Branched alkenes are preferably used. In contrast to the conventional processes, mixtures of alkenes, and if desired of alkenes with alkanes, as formed, for example, in the cracking or dehydrogenation of hydrocarbons, eg. petroleum, or the oligomerization of olefins, in particular of isobutylene, propylene and n-butane, or the hydrogenation of carbon monoxide, may also advantageously be used.

Examples of olefins which may be used as starting materials II are 2-methylpent-1-ene, 2-ethylpent-1-ene, 2-propylpent-1-ene, 2-methylhex-1-ene and 2-ethylhex-1-ene, and the corresponding alkenes which are substituted in the 1-, 3- or 4-position by methyl, ethyl, n-propyl, isopropyl, n-butyl, isobutyl, sec.-butyl or tert.-butyl; 2,3,3-trimethylbut-1-ene, 2-ethyl-3,3-dimethylbut-1-ene, 2,3,3-trimethylhept-1-ene, 2,4,4-trimethylpent-1-ene, 2,3,3-trimethylpent-1-ene and 2,3,4-trimethylpent-1-ene, and the corresponding alkenes with the double bond in the 2-position in the molecule; branched alkenes, as obtained in the form of mixtures in the dimerization of isobutylene or n-butene (octenes) or the trimerization of isobutylene or n-butene (dodecenes) or of propylene (nonenes) or the tetramerization of propylene (dodecenes); α-methylstyrene, o-methylstyrene, m-methylstyrene, p-methylstyrene, 3,5-dimethylstyrene, o-ethylstyrene, m-ethylstyrene, p-ethylstyrene, 4-chlorostyrene, cycloheptene, 1-methylcyclohex-1-ene and benzonorbenene. Preferred compounds are isobutylene, styrene, 2,3-dimethylbut-1-ene, 2-methylbut-1-ene, 2-methylbut-2-ene, 2-ethylbut-1-ene, cyclopentene, cyclohexene, α-methylstyrene, norbornene, 2-ethylhex-1-ene, 2-ethylhex-2-ene, diisobutene (2,4,4-trimethylpent-1-ene), 1-methylcyclohex-1-ene, camphene and dicyclopentadiene.

Examples of suitable carbamates II are methyl, ethyl, propyl, isopropyl, benzyl, butyl, isobutyl, octyl, cyclohexyl, cyclopentyl and n-hexyl carbamates.

The alcohol is used an amount of from 0.1 to 50, in particular from 0.5 to 20, g per mole of carbamate II. Suitable alcohols are those of the formula $$R^5OH \qquad \qquad IV$$

where $R^5$ has the above general and preferred meanings, but the alcohol on which the carbamate II is based is preferably used.

The reaction is carried out in general at from 25° to 160° C., preferably from 40° to 150° C., in particular from 60° to 130° C., under reduced pressure, superatmospheric pressure or, advantageously, atmospheric pressure, either continuously or batchwise. The residence time is preferably from 0.5 to 10, in particular from 0.5 to 5, hours. Advantageously, no additional solvent is employed.

The catalysts employed are organic cation exchangers containing sulfonic acid groups, and it is advantageous to use resins obtained from sulfonated polystyrene-divinylbenzene or sulfonated, crosslinked styrene polymers, or phenol-formaldehyde or benzene-formaldehyde resins containing sulfonic acid groups, or copolymers of tetrafluoromethylene and vinylsulfonyl fluoride. Sulfonated polystyrene-divinylbenzene exchangers are preferred. The exchanger is present in the acid form and not as the salt. The catalyst can have either a macroporous or a gel-like structure, and advantageously has a particle size of from 5 to 2,000 μm, preferably from 10 to 1,500 μm. In the case of gel-like catalysts, the particle size is, in particular, from 10 to 200 μm, and the total specific surface area is from 10 to 300 m²/g, while in the case of macroporous catalysts the inner specific surface area is, in particular, from 10 to 200 m²/g. Examples of suitable exchanger resins are those obtainable commercially under the names ®LEWASORB AC-10, ®Amberlyst-15, ®LEWATIT SPC-118, ®LEWATIT SPC-108 and ®Nafion. They are advantageously dehydrated, before use, in a conventional manner, for example by heating at from 100 to 110° under reduced pressure. However, dehydration may also be effected by displacing water with hydrophilic organic liquid and then heating at 100° C. under reduced pressure, or by azeotropic distillation with an organic liquid.

The catalyst, in the form of an ion exchanger, can be used in any desired batchwise or continuous procedure, for example as a fixed bed. It is advantageously present in suspension during the reaction, as a rule in the reaction mixture being formed. Advantageously, a proportion of the liquid carbamate II and olefin III is initially taken, and the catalyst is suspended in the thoroughly stirred mixture. From 3 to 100, in particular from 5 to 50, g of ion exchanger are preferably employed per mole of carbamate II. Advantageously, the reaction mixture is mixed thoroughly during the entire reaction, preferably at a velocity of not less than 100, advantageously from 200 to 2,000, in particular from 300 to 1,000, rpm. Preferred mixing apparatuses without stirrers, for example including apparatuses where mixing is effected by means of an inert gas, eg. nitrogen, are those which are capable of a shear force corresponding to the above mixing velocity. In this manner, a finely dispersed suspension is obtained.

The reaction can be carried out as follows: a mixture of starting materials II and III, catalyst and alcohol IV is kept at the reaction temperature during the reaction time. After the catalyst has been separated off, the end product can be isolated in a conventional manner, for example by filtration and distillation.

Where the catalyst used is an ion exchanger, and the process is effected continuously, the reaction may be carried out in a fixed bed, or advantageously as follows: a liquid mixture of carbamate, olefin and alcohol is passed, at the reaction temperature and reaction pressure, through a suspension of the catalyst in starting mixture or reaction mixture, and the mixture is then filtered. The end product is then isolated from the reaction mixture in a conventional manner, for example by distillation. The filtration is advantageously carried out before the suspension leaves the reactor. Suitable filters are acid-resistant filter cloths, wire gauze filters and sintered metal filters, provided that the mesh size or pore diameter is smaller than the catalyst particle.

The N-substituted carbamates I obtainable by the process of the invention are active ingredients and useful starting materials for the preparation of dyes, pesticides and drugs. By hydrolysis of the carbamates (Houben-Weyl, volume 11/1, pages 948-952), the corresponding amines can be prepared, these likewise being important starting materials in the synthesis of active ingredients. Regarding the use of these compounds, reference may be made to the stated publications and to Ullmanns and Encyklopädie der technischen Chemie, volume 5, pages 73-76.

EXAMPLE 1

A stirred mixture of 89 g of ethyl carbamate, 5 g of ethanol, 10 g of ®LEWASORB AC-10 and 70 g of isobutene was heated to 70° C. in a stirred autoclave, and stirring was continued at this temperature for 4 hours. After the reaction was complete, the catalyst was separated off and the mixture was worked up by distillation. 136 g (93% of theory) of ethyl N-tert.-butylcarbamate of boiling point 70°-71° C./20 mbar were obtained. Gas chromatography showed that the crude product contained 0.2 percent by weight of diisobutene, but not diethyl carbonate was detected.

EXAMPLE 2

A stirred mixture of 117 g of butyl carbamate, 5 g of butanol, 15 g of ®LEWASORB AC-10 and 60 g of isobutene was heated to 70° C. in a stirred autoclave, and stirring was continued at this temperature for 4 hours. Thereafter, the catalyst was separated off and the mixture was distilled under reduced pressure. 161 g (93% of theory) of butyl N-tert.-butylcarbamate of boiling point 110°-111° C./20 mbar were obtained. No substantial amount of diisobutene was detected.

EXAMPLES 3-7

The catalyst employed in Example 2 was also used in the reaction below, which were carried out similarly to Example 2.

|  | Yield (% of theory) |
| --- | --- |
| Example 3 | 94 |
| Example 4 | 89 |
| Example 5 | 90 |
| Example 6 | 93 |
| Example 7 | 92 |

The product contained 0-0.2 percent by weight of diisobutene, but no carbonates were detected.

EXAMPLE 8

A stirred mixture of 117 g of butyl carbamate, 5 g of butanol, 17 g of ®LEVATIT SPC-118 and 160 g of a mixture comprising 49 percent by weight of isobutene, 41.5 percent by weight of n-butenes and 9.5 percent by weight of butanes was heated to 70° C. in a stirred autoclave, and stirring was continued at this temperature for 5 hours. Thereafter, the catalyst was separated off and the mixture was distilled under reduced pressure. 149 g (86% of theory) of butyl N-tert.-butylcarbamate of boiling point 110°-111° C./20 mbar were obtained. No substantial amount of diisobutene was detected.

LEWATIT SPC-118 is a commercially available, macroporous cation exchanger which contains sulfonic acid groups, is based on a 82:18 styrene-divinylbenzene copolymer and has a particle size of from 30 to 1,500 $\mu$m and an inner specific surface area of 40 m$^2$/g.

EXAMPLE 9

A stirred mixture of 178 g of ethyl carbamate, 94 g of norbornene, 5 g of ethanol and 20 g of ®LEWASORB AC-10 was heated to 70° C. in a stirred reactor, and stirring was continued at this temperature for 7 hours. Thereafter, the catalyst was filtered off and the mixture was distilled under reduced pressure. 157 g (86% of theory) of ethyl N-norbornylcarbamate of boiling point 148°-150° C./20 mbar and melting point 50° C. (from pentane) were obtained. No substantial amount of norbornene oligomers was detected.

EXAMPLE 10 (COMPARATIVE EXAMPLE)

A stirred mixture of 89 g of ethyl carbamate, 10 g of ®LEWATIT SC-108 and 70 g of isobutene was heated to 70° C., and stirring was continued at this temperature for 4 hours. After the reaction was complete, the catalyst was separated off and the reaction mixture was analyzed by gas chromatography. It contained, in addition to unreacted starting materials, 41 g (28% of theory) of ethyl N-tert.-butylcarbamate and 2 g of diisobutene.

®LEWATIT SC-108 is a commercially available, gel-like cation exchanger which contains sulfonic acid groups, is based on a 92:8 styrene-divinylbenzene copolymer and has a particle size of from 300 to 1,500 $\mu$m.

EXAMPLE 11 (COMPARATIVE EXAMPLE)

A stirred mixture of 89 g of ethyl carbamate, 10 g of ®LEWASORB AC-10 and 70 g of isobutene was heated to 70° C. in a stirred autoclave, and stirring was continued at this temperature for 4 hours. After the reaction was complete, the catalyst was separated off and the reaction mixture was analyzed by gas chromatography. It still contained 4.5 percent by weight of diisobutene, in addition to the end product. Distillation of the crude product gave 134 g (92% of theory) of ethyl N-tert.-butylcarbamate of boiling point 70°–71° C./20 mbar.

®LEWASORB AC-10 is a commercially available, gel-like cation exchanger which contains sulfonic acid groups, is based on a 92:8 styrene-divinylbenzene copolymer and has a particle size of from 10 to 200 μm.

We claim:

1. A process for the preparation of an N-substituted carbamate of the formula

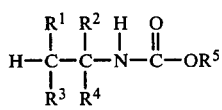   I where the individual radicals $R^1$, $R^2$ and $R^3$ may be identical or different and $R^2$ is always an aliphatic, cycloaliphatic, araliphatic or aromatic radical, $R^4$ is an aliphatic, cycloaliphatic or araliphatic radical or, when $R^2$ is an aromatic radical or a member of an alicyclic, bicyclic or tricyclic radical, may furthermore be hydrogen, 2 or more of the radicals $R^1$, $R^2$, $R^3$ and $R^4$ may furthermore be members of an alicyclic, bicyclic or tricyclic radical, $R^1$ and/or $R^3$ may furthermore be hydrogen, and $R^5$ is an aliphatic, cycloaliphatic or araliphatic radical, by reaction of a carbamate with an olefin in the presence of an organic cation exchanger containing sulfonic acid groups, as the catalyst, wherein a carbamate of the formula

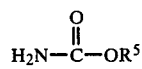   II where $R^5$ has the above meanings, is reacted with an olefin of the formula

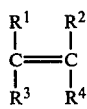   III where $R^1$, $R^2$, $R^3$ and $R^4$ have the above meanings, in the presence of from 0.1 to 50 g of an alcohol per mole of starting material II.

2. A process as claimed in claim 1, wherein the reaction is carried out using from 0.3 to 5 moles of olefin III per mole of carbamate II.

3. A process as claimed in claim 1, wherein the reaction is carried out using from 0.5 to 20 g of an alcohol per mole of carbamate II.

4. A process as claimed in claim 1, wherein the reaction is carried out at from 25° to 160° C.

5. A process as claimed in claim 1, wherein the reaction is carried out at from 40° to 150° C.

6. A process as claimed in claim 1, wherein the reaction is carried out during a residence time of from 0.5 to 10 hours.

7. A process as claimed in claim 1, wherein the reaction is carried out using, as a catalyst, a sulfonated polystyrene-divinylbenzene exchanger.

8. A process as claimed in claim 1, wherein the reaction is carried out using a catalyst with a particle size of from 5 to 2,000 μm.

9. A process as claimed in claim 1, wherein the reaction is carried out using a gel-like catalyst with a particle size of from 10 to 200 μm.

10. A process as claimed in claim 1, wherein the reaction is carried out using a catalyst with a total specific surface area of from 10 to 300 m²/g.

11. A process as claimed in claim 1, wherein the reaction is carried out using from 3 to 100 g of ion exchanger per mole of carbamate II.

12. A process as claimed in claim 1, wherein the reaction is carried out using, as a catalyst, an organic cation exchanger selected from the group consisting of sulfonated polystyrene-divinylbenzene resins, sulfonated crosslinked styrene polymers, phenol-formaldehyde or benzene formaldehyde resins containing sulfonic acid groups, and copolymers of tetrafluoroethylene and vinylsulfonyl fluoride.

13. A process as claimed in claim 1, wherein the reaction is carried out using an alcohol of the formula $R^5OH$   IV where $R^5$ is an aliphatic, cycloaliphatic or araliphatic radical.

14. A process as claimed in claim 1, wherein the reaction is carried out using an alcohol of the formula $R^5OH$   IV where $R^5$ is alkyl of 1 to 10 carbon atoms, cycloalkyl of 5 to 8 carbon atoms or aralkyl of 7 to 12 carbon atoms.

15. A process as claimed in claim 1, wherein the reaction is carried out using an alcohol of the formula $R^5OH$   IV where $R^5$ is identical in formula II and formula IV.

16. A process as claimed in claim 15, wherein the reaction is carried out using from 0.5 to 20 g of the alcohol IV per mole of carbamate II.

17. A process as claimed in claim 16, wherein the reaction is carried out at from 25° to 160° C. using from 0.3 to 5 moles of olefin III per mole of carbamate II.

18. A process as claimed in claim 17 wherein the reaction is carried out using, as a catalyst, an organic cation exchanger selected from the group consisting of sulfonated polystyrene-divinylbenzene resins, sulfonated crosslinked styrene polymers, phenol-formaldehyde or benzene-formaldehyde resins containing sulfonic acid groups, and copolymers of tetrafluoroethylene and vinylsulfonyl fluoride.

19. A process as claimed in claim 18 wherein the reaction is carried out, using as a catalyst, a sulfonated polystyrene-divinylbenzene exchanger.

20. A process as claimed in claim 18 wherein the reaction is carried out using from 3 to 100 g of ion exchanger per mole of carbamate II.

* * * * *